United States Patent [19]

Ansari et al.

[11] Patent Number: 4,606,849
[45] Date of Patent: Aug. 19, 1986

[54] PERFUMERY COMPOSITIONS

[75] Inventors: Hifzur R. Ansari, Montvale, N.J.; Alfred A. Schleppnik, St. Louis, Mo.

[73] Assignee: Bush Boake Allen Limited, London, England

[21] Appl. No.: 695,891

[22] Filed: Jan. 29, 1985

[30] Foreign Application Priority Data

Feb. 1, 1984 [GB] United Kingdom ............... 8402641

[51] Int. Cl.$^4$ ............................................. A61K 7/46
[52] U.S. Cl. ................................... 252/522 R; 549/333
[58] Field of Search .................... 252/522 R; 549/333

[56] References Cited

U.S. PATENT DOCUMENTS 3,901,920  8/1975  Lesher et al. ..................... 549/333
4,113,664  9/1978  Conrad et al. ................. 252/522 R

OTHER PUBLICATIONS

Ansari et al., Chemical Abstract, vol. 104 (3) 19594 (1985).
Nippon Petro Chem., Chemical Abstracts, vol. 96 (23) 199664e (1982).

*Primary Examiner*—Werren B. Lone
*Attorney, Agent, or Firm*—Kane, Dalsimer, Kane, Sullivan and Kurucz

[57] ABSTRACT

3,3-Dimethyl-1,5-dioxaspiro [5,5] undecane is useful in perfumery compositions. It can be made economically by reaction of cyclohexanone with neopentyl glycol in the presence of an acid, generally paratoluene sulphonic acid, under dehydrating conditions, generally by refluxing with a non-polar solvent.

7 Claims, No Drawings

PERFUMERY COMPOSITIONS

This invention relates to compounds of value as synthetic perfumery compounds.

If a compound is to serve as a synthetic perfumery compound it has to comply with three essential requirements and failure of any of these requirements will prevent it being a useful synthetic perfumery compound.

One requirement is that the compound has, at low concentrations, a pleasant odour and can be blended with other perfumery compounds to give pleasant blended odours.

Another requirement is that it is stable in compositions in which it can be used commercially, for instance when in soap or shampoo its odour and other properties must not change on storage.

The third requirement is that the compound must be capable of being synthesized at low cost from readily available starting materials. There is little or no commercial interest in compounds as synthetic perfumery compounds if their synthesis requires expensive and poorly available starting materials or if it requires expensive process steps, since the reason for providing synthetic perfumery compounds is to get away from the expense of natural perfumery compositions.

Most of the thousands or millions of low molecular weight aliphatic compounds have an odour but, despite this, very few of them are useful as synthetic perfumes since very few have the required combination of useful odour characteristics (especially when blended), stability to compositions in which they can be used (e.g. soaps), and low cost.

There is a continuing demand for new synthetic perfumery compounds, especially compounds that are easy to make economically and that have perfumery properties that render them very valuable for use in a wide range of perfumery compositions.

The ketal formed between propylene glycol and 2-methylcyclohexanone (Heridone) is known as a useful odiferous chemical. Unfortunately, the methyl substitution in the cyclohexyl ring increases its cost and reduces its availability. It is generaly found that alkyl substitution into, for instance, a cyclohexyl ring has a very significant effect on the odiferous properties and that decreasing the alkyl substitution detracts from the perfumery qualities of the compound.

Despite this we have now surprisingly found that the ketal of neopentyl glycol (2,2-dimethyl propane-1,3-diol) with cyclohexanone has very useful perfumery properties. We have also found that this compound is easily made in good yields from readily available materials. Accordingly this compound meets the need for a relatively cheap and readily available odiferous compound having perfumery qualities that permits its usage in large quantities in perfumery compositions.

It is particularly surprising that this compound has useful perfumery properties as we have found that certain other ketals of unsubstituted cyclohexanone (in particular the ketals with ethylene glycol, propane-1,2-diol, butane-1,3-dioil and 2-methyl-2,4-pentane diol) have little or no valuable odiferous properties.

The compound used in the invention has the structural formula I below:

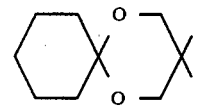

and has the name 3,3-dimethyl-1,5-dioxaspiro [5,5] undecane.

A perfumery composition according to the invention comprises the compound of Formula I and a carrier of the type conventionally present in perfumery compositions. Generally the composition includes at least one other odiferous chemical compound and generally includes a large number of such compounds. The composition may take the form of a perfumery concentrate for incorporating in a consumer composition. The concentrate may contain 0.1 to 40%, for instance 3 to 30%, by weight of the compound of Formula I. Often the composition contains at least 5%, and often at least 10%, by weight of the compound of Formula I.

Consumer compositions according to the invention can be one of a wide variety of typical perfumed compositions but preferably take the form of shampoos, creams, lotions, room sprays, cleansers, soaps and detergents. Particularly preferred compositions are alkaline compositions such as bleach, alkaline cleaner, soaps and alkaline detergents because an advantage of the compound of formula I is that it has good stability at high pH values. Generally the composition has a pH of from 4 to 13, preferably 7 to 11.5.

In addition to having good stability, both as regards colour and odour, at a wide variety of high pH values and especially at high pH values the compound has the advantage that it has relatively low volatility.

The odour of the compound has fresh, thyme, sweet, medicinal, slightly minty characteristics and its inclusion in a composition does not result in discolouration of that composition.

The compound of formula I is best made by reaction of cyclohexanone with neopentyl glycol. This reaction can be conducted in the presence of an organic silicon compound, for instance in a manner similar to that described in Chemical Abstracts 97, 109945r.

Preferably the compound is made by reacting neopentyl glycol with cyclohexanone in the presence of an acid under dehydrating conditions. The acid is preferably a strong acid, most preferably paratoluene sulphonic acid. The reaction water should be removed, preferably during the reaction, for instance by distillation. Thus the reaction may be effected by refluxing the reaction mixture for as long as is necessary to remove all the water. Preferably the reaction is conducted in an inert inorganic solvent, generally a non-polar solvent such as an aromatic hydrocarbon. The preferred process therefore comprises refluxing the mixture of cyclohexanone, neopentyl glycol and non-polar solvent until substantially all the water has been eliminated. Reflux is preferably at ambient pressure.

Example 1 illustrates the synthesis of the compound and Example 2 a perfumery concentrate containing it.

EXAMPLE 1

A mixture of neopentyl glycol (179 grams), cyclohexanone (145 grams), toluene (300 mls) and p-toluene sulphonic acid (0.85 grams) is stirred under reflux, removing water via a Dean and Stark head. When no more water is obtained, the reaction is cooled and washed free of acid with aqueous sodium carbonate solution. The organic layer is then fractionated to obtain 242 grams of the compound of Formula I (89% of the theoretical yield), boiling point 90° C. at 10 Torr.

EXAMPLE 2

A fruity jasmin perfumery concentrate was formulated by blending the following ingredients:

|  | by weight |
| --- | --- |
| Benzyl Acetate | 45.00 |
| Hexyl Cinnamic Aldehyde | 10.00 |
| $C_{14}$ Aldehyde (10% in DPG) | 2.00 |
| $C_{18}$ Aldehyde (10% in DPG) | 2.00 |
| Cyclamen Aldehyde | 0.50 |
| Cis Jasmin | 0.30 |
| Ylang 6780 | 2.00 |
| Linalol (Pure) | 1.00 |
| Benzyl Benzoate | 5.00 |
| Geranyl Butyrate | 2.50 |
| Citronellyl Butyrate | 0.80 |
| Raspberry Ketone (10% in DPG) | 1.50 |
| Dimethyl Benzyl Carbinyl Acetate | 1.50 |
| Dipropylene Glycol (Deodorised) | 15.90 |
| Compound of Formula I | 10.00 |
|  | 100.00 |

We claim:

1. A perfumery composition comprising 3,3-dimethyl-1,5-dioxaspiro [5,5] undecane and a perfumery composition carrier.

2. A composition according to claim 1 including at least one other odiferous compound.

3. A composition according to claim 1 which comprises 3 to 40% by weight of 3,3-dimethyl-1,5-dioxaspiro [5,5] undecane and that is a perfumery concentrate that can be incorporated into a consumer composition.

4. A composition according to claim 1 that is a consumer composition selected from shampoos, creams, lotions, room sprays, cleansers, soaps and detergents.

5. A process in which 3,3-dimethyl-1,5-dioxaspiro [5,5] undecane is made by reacting cyclohexanone with neopentyl glycol in the presence of an acid under dehydrating conditions.

6. A process according to claim 5 in which the acid is paratoluene sulphonic acid.

7. A process according to claim 5 conducted by refluxing cyclohexanone, neopentyl glycol and a nonpolar solvent in the presence of paratoluene sulphonic acid.

* * * * *